US005556378A

United States Patent [19]
Storz et al.

[11] Patent Number: 5,556,378
[45] Date of Patent: Sep. 17, 1996

[54] DEVICE FOR IRRIGATION OF BODY CAVITIES

[76] Inventors: Karl Storz, Auf dem Schildrain 39, 78532 Tuttlingen, Germany; Pavel Novak, Stettemerstr, 117, CH-8207 Schaffhausen, Switzerland

[21] Appl. No.: 308,251

[22] Filed: Sep. 19, 1994

Related U.S. Application Data

[63] Continuation-in-part of Ser. No. 77,720, Jun. 17, 1993, abandoned.

[30] Foreign Application Priority Data

Jun. 17, 1992 [DE] Germany ................. 42 19 890.0

[51] Int. Cl.[6] .................................................. A61M 1/00
[52] U.S. Cl. ................................. 604/31; 604/153
[58] Field of Search ................... 604/22, 31, 35, 604/118, 51, 65–67, 153; 128/DIG. 12

[56] References Cited

U.S. PATENT DOCUMENTS

| | | | |
|---|---|---|---|
| 3,410,268 | 11/1968 | Leucci | 604/31 |
| 3,900,022 | 8/1975 | Widran | 604/118 |
| 4,024,866 | 5/1977 | Wallach | 604/31 |
| 4,041,947 | 8/1977 | Weiss et al. | 604/118 |
| 4,168,707 | 9/1979 | Douvas et al. | 604/31 |
| 4,261,360 | 4/1981 | Perez | 604/31 |
| 5,098,387 | 3/1992 | Wiest et al. | 604/31 |
| 5,213,571 | 5/1993 | Fujio et al. | 604/31 |

*Primary Examiner*—John D. Yasko
*Assistant Examiner*—Mark Bockelman
*Attorney, Agent, or Firm*—Antonelli, Terry, Stout & Kraus

[57] ABSTRACT

A device for the irrigation and suction drainage of body cavities, especially in surgical laparoscopy, hysteroscopy, uroscopy, or arthroscopy. The device comprises two conventional pumps, each being equipped with a pressure sensor and being preferably designed as rotary tube pumps. The irrigation pump and the suction drainage pump are connected with each other by way of a control line, and they operate in a master-slave mode. Operation is very simple, in that only the irrigation pump needs to be adjusted and operated by the operator. Control of the suction drainage pump takes place automatically based on the measured values of both pressure sensors in the irrigation and suction drainage conduits and the set r.p.m.'s of the irrigation pump. The primary advantage of the device resides in that the suction drainage pump takes care automatically of uniform pressure and flow relationships at the site of the surgery independently of the adjustment of the irrigation pump.

20 Claims, 3 Drawing Sheets

DEVICE FOR IRRIGATION OF BODY CAVITIES

This application is a continuation-in-part of U.S. application Ser. No. 08/077,720, filed Jun. 17, 1993 now abandoned, which application is incorporated herein by reference.

TECHNICAL FIELD

The invention relates to a device for the irrigation of body cavities. Such devices are needed, for example, in surgical laparoscopy, hysteroscopy, uroscopy, or arthroscopy.

BACKGROUND ART

A device of this type has been known from the article by S. F. Zakko, A. F. Hofmann, "Microprocessor-Assisted Solvent Transfer System for Effective Contact Dissolution of Gallbladder Stones", IEEE Transactions on Biomedical Engineering, vol. 37, No. 4, April 1990. This conventional device exhibits two pumps, one of these operating as an irrigation pump and the other as a suction pump. Via conduits and via ducts and/or conduits leading into the respective body cavity which can be provided, in particular, in an endoscopic instrument, these pumps are connected to the body cavity to be irrigated so that a simultaneous irrigation and suction drainage operation can be performed. Furthermore, a pressure sensor unit and a control unit are included, regulating the two pumps via a control line.

The conventional device has the drawback that, for the simultaneous performance of the irrigation and suction drainage step, two pumps are utilized operating independently of each other, i.e. each having its own drive means, so that control is costly.

Furthermore, usually an additional line is required for process monitoring and control, this line leading into the respective body cavity. By means of this third line, necessitating a triple lumen catheter, the pressure ambient at the target site is detected and employed for regulating the irrigation. Such a line either requires an additional puncture, or this line occupies additional space within the endoscope shank.

DE 39 33 856 A1 discloses a device for the irrigation and suction drainage of body cavities which comprises a pressure pump and a suction pump and hose lines connected to these pumps leading to the body cavity. Operation of this device requires a vacuum pump arranged in the control line and a special drive motor connected, via a switch-over gear system, with the two pumps. With the aid of an expensive control circuit, the joint drive motor is operated either in left-handed operation, i.e. irrigation, or in right-handed operation, for suction purposes. Thus, irrigation fluid is alternatingly fed and discharged. It is impossible with such a device to produce a higher fluid throughput without marked pressure fluctuations.

DE 38 13 266 A1 describes another device for irrigating body cavities, consisting of an instrument that can be inserted in the corresponding body cavity, exhibiting only one duct for the irrigation and drainage fluid, and of a conveying means designed as a pump with reversible direction of delivery. The aforementioned disadvantages apply to this device in the same way.

DISCLOSURE OF INVENTION

It is an object of the invention to provide a device for the irrigation of body cavities wherein the irrigation process and, in particular, the suction drainage process are controlled with high functional safety and a low space requirement for the ducts leading into the body cavity, in such a way that a constant excess pressure is produced within the respective body cavity.

According to the invention, the pressure sensor unit comprises two pressure sensors, one of which detects the pressure of the irrigation pump and the other of which picks up the pressure of the suction drainage pump, the output signals of these sensors being applied to the control unit. The control unit regulates the two pumps in master-slave operation in such a way that, after adjustment of the irrigation pump by an operator, the suction drainage pump is controlled based on the output signals of the pressure sensors as well as the set r.p.m. of the irrigation pump.

Expressed differently, the device of this invention consists of two pumps each equipped with a pressure sensor. The pumps can be designed preferably as a peristaltic pump. The irrigation pump and the suction drainage pump, are connected to each other by way of a control line and work in a master-slave operation. Operation is very simple in that, in a customary fashion, only the irrigation pump needs to be adjusted and operated by the operator. Control of the suction drainage pump takes place automatically based on the measured values from both pressure sensors in the irrigation and drainage conduits, as well as based on the set r.p.m. of the irrigation pump. When the flow resistance has been measured, it is possible to also detect the pressure within the body cavity based on the two measured pressure values.

The primary advantage of the invention is that the suction drainage pump automatically provides uniform pressure and flow relationships at the site of the surgery independently of the adjustment of the irrigation pump.

The occurrence of an error, which can arise predominantly by clogging of the suction line, is detected by the invention by the fact that, in spite of rising pressure in the irrigation line, the pressure in the suction line becomes increasingly lower, with the speed of revolution of both pumps remaining the same.

A further improvement in functional safety can be attained by an additional weighing unit, by means of which the weight of the irrigation fluid storage container as well as of the irrigation fluid collection container can be correspondingly balanced. However, in this case it must be ensured that no irrigation fluid can escape, for example, through leakage sites.

BRIEF DESCRIPTION OF DRAWINGS

The invention will be described in greater detail below with reference to an embodiment; in the appended drawings.

BEST MODE FOR CARRYING OUT THE INVENTION

Figure 1:
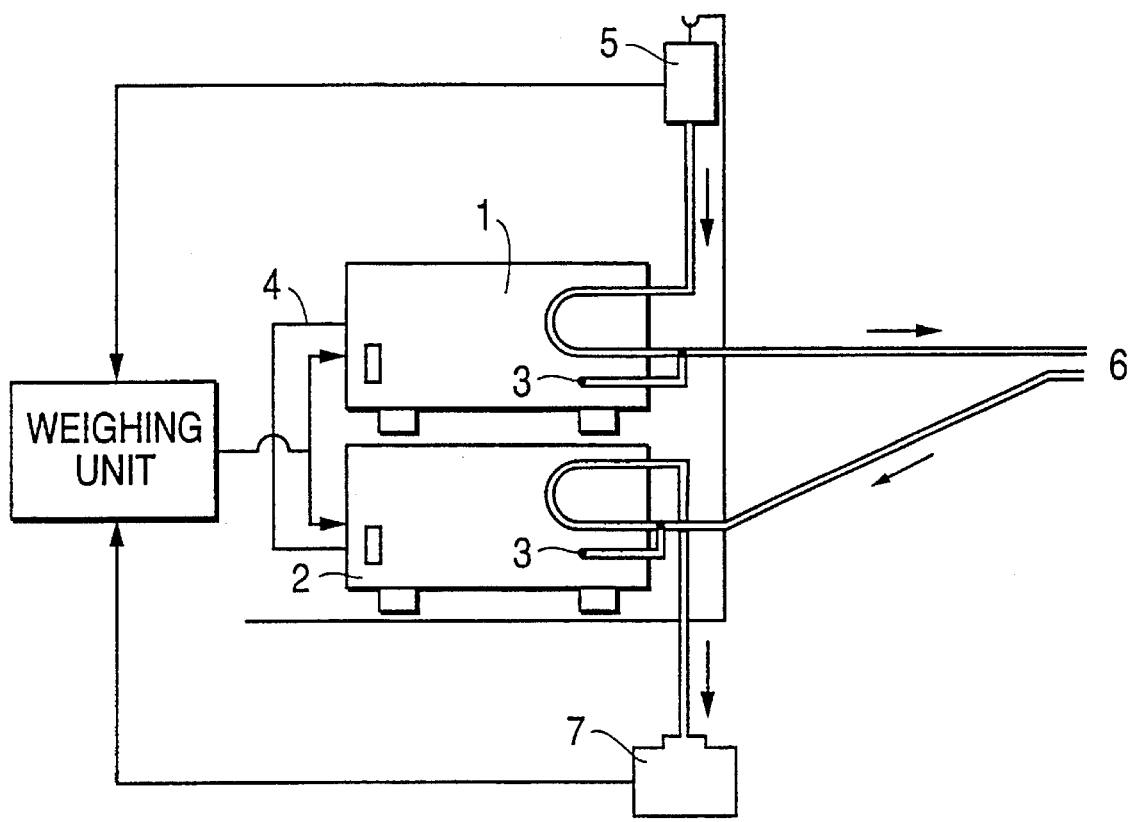
FIG. 1 shows the structure of an embodiment of the invention.

FIG. 1 illustrates a device in accordance with the invention for irrigating body cavities which comprises two pumps, namely an irrigation pump 1 and a suction drainage pump 2, arranged in an integrated unit. The two pumps are connected by way of conduits and ducts located in an instrument with a body cavity 6. Pressure sensors 3 are installed in the irrigation and suction drainage lines. The output signals from the pressure sensors 3 are applied to the control unit within the housings of the pumps 1 and 2. The sensors are arranged in an intermediate zone of the pumps.

As illustrated in FIG. 1, the pressure sensors detect pressure in the irrigation and suction drainage lines.

The control unit regulates the suction drainage pump to have a settable pressure in a suction drainage conduit.

The pumps are peristaltic pumps.

The control unit can have the flow resistance of the ducts and conduits independently fed to the control units. The flow resistance may be derived from the output signals of the two pressure sensors 3 and from the irrigation flux which is proportional to the r.p.m. of the peristaltic irrigation pump, as long as there is no leakage within the body cavity. The flow resistance may be derived from the r.p.m. of peristaltic irrigation and suction pumps.

A weighing unit 8 may be used to detect a weight difference between the storage container 5 for the irrigation fluid and the collection container 7 for the suction drained fluid with a control signal from the weighing unit being applied to the control unit for balancing the weight of the containers 5 and 7.

The control units of the two pumps are connected with each other through a control line 4 wherein the control unit of the irrigation pump dominates over the control unit of the suction drainage pump in a master-slave relationship.

The operating cycle can be derived from the illustrated arrows. The irrigation fluid is removed from the irrigation fluid storage container 5 by means of the irrigation pump 1 and transported into the patient's body cavity 6 to be supplied.

The suction drainage pump 2 ensures that the irrigation fluid is drained by suction from the body cavity 6 in accordance with a mode that can be set by the operator, and is conveyed to the irrigation fluid collection container 7.

The operator, in this process, merely adjusts the irrigation pump 1 so that a specific pressure value, for example 100 mm Hg, is obtained in the irrigation line. The control unit of the suction pump then sets the r.p.m. of the suction drainage pump 2 based on the measured values of the two pressure sensors 3 and the adjusted r.p.m. of the irrigation pump so that a certain pressure, e.g. 40 mm Hg, is reached in the suction drainage line.

Figure 2:
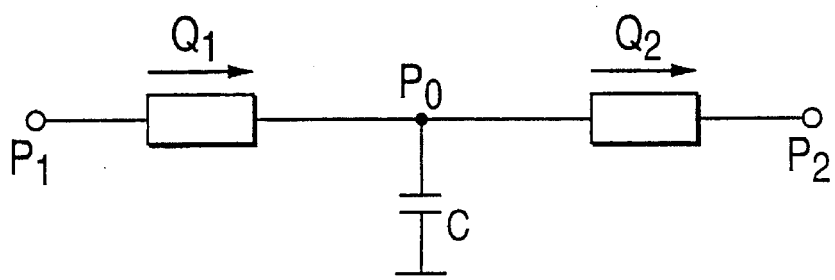
FIG. 2 shows a schematic illustration of the apparatus according to FIG. 1 and this invention.

FIG. 2 shows a schematic illustration of the scheme of the fluid system between the irrigation and the suction pump, which encloses the irrigation, suction line and the body cavity. These components are represented by the flow resistance, respectively volume-capacity. As long as the device is not leaky, the irrigation flux $Q_1$ must equal the suction flux $Q_2$ so that a constant pressure $P_o$ is produced within the patient. The system can be described by the following equations:

$$Q_1 = \frac{P_1 - P_o}{R_1}, \quad Q_2 = \frac{P_o - P_2}{R_2}, \quad P_o = \frac{(Q_1 - Q_2)\Delta t}{C}$$

with Po being the change of the pressure within the patient during time $\Delta t$ and $R_1$, $R_2$ and C are respectively the flow resistance in the irrigation line, the flow resistance in the suction line and the capacity of the body to retain the irrigation flux $Q_1$. The flow resistance may be derived from the r.p.m. of peristaltic irrigation and suction drainage pumps.

Figure 3:
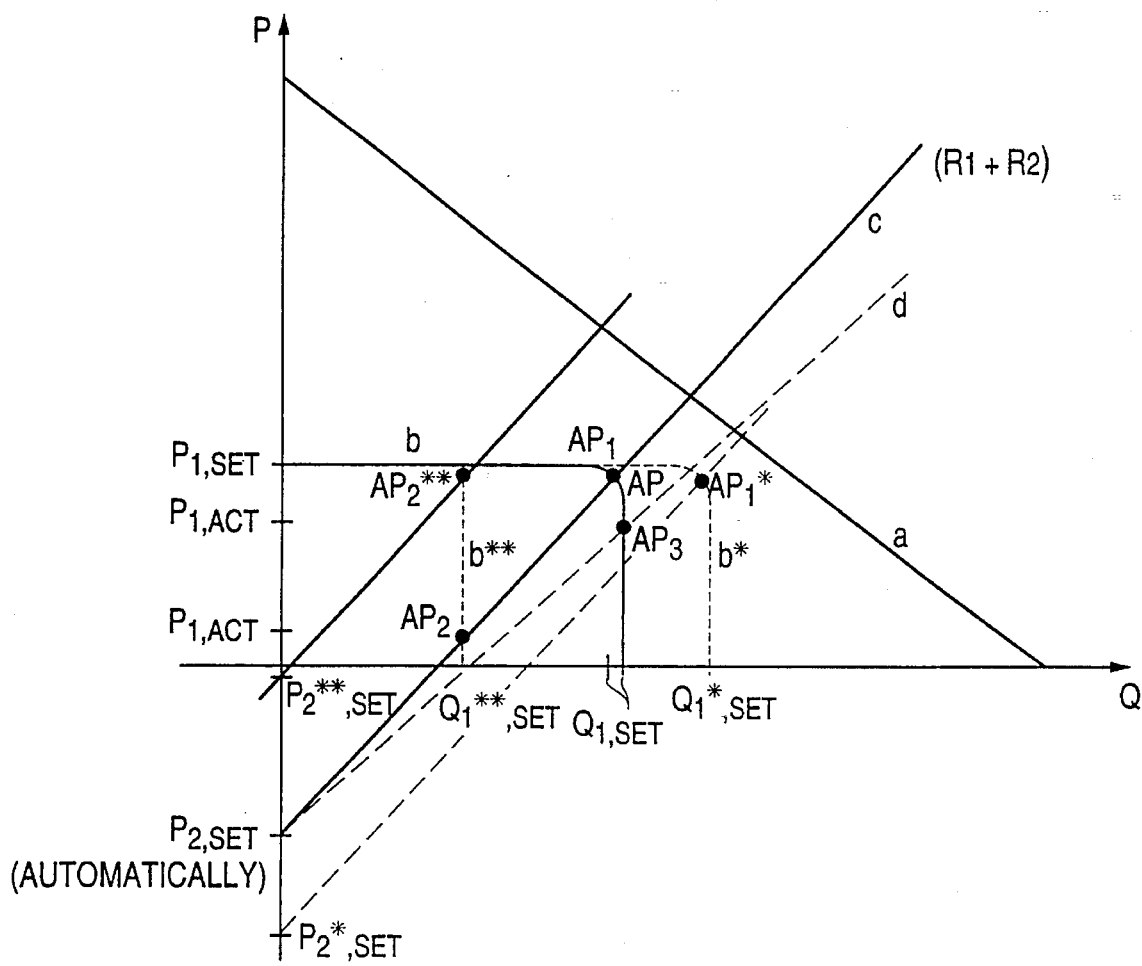
FIG. 3 shows a simplified schematic illustration of the characteristic line of a pump in accordance with the invention.

In FIG. 3 a simplified schematic illustration of the characteristic line of a pump is shown. In case of a real pump, the characteristic line doesn't have to be linear which is also caused by the type of the pump.

It is now important to achieve that the irrigation ($P_1$, $Q_1$) and the suction ($P_2$, $Q_2$) are regulated in a way that the pressure $P_o$ within the patient stays constant. The fluxes $Q_1$ and $Q_2$ are proportional to the r.p.m. of the irrigation and suction drainage pumps 1 and 2.

a: pressure regulation

In case that only the pressures $P_1$ and $P_2$ are regulated, $P_1$ mainly determines the pressure $P_0$ within the patient; on the other hand, with the suction pressure $P_2$ the flow can be varied:

$$Q = Q_1 = Q_2 = \frac{P_1 - P_2}{R_1 + R_2}$$

According to the adjustment of $P_1$ and $P_2$, a pressure within the patient of $$P_o = P_2 - R_1 \frac{P_1 - P_2}{R_1 - R_2}$$

is attained.

When a doctor wants to change the adjusted pressure within the patient, he has the ability to manipulate either $P_1$ or $P_2$ which, however, at the same time changes the flow Q.

In case of an interruption of the irrigation step, the irrigated organ would be emptied completely; moreover, a low pressure $P_o = P_2$ could be produced.

If, on the other hand, the suction drainage step is interrupted, the pressure within the patient $P_o$ will increase up to the value $P_2$. The difference $P_1 - P_o$ does not exceed 30–50 mmHg depending on the chosen irrigation flux and the tube and instruments parameters which are used. This increase is not very high, but it could possibly lead to the injury of the patient if the increase lasts too long.

b: pressure and flow regulation

If, however, on the irrigation side a pump is used which is able to regulate the pressure $P_1$ as well as the irrigation flux $Q_1$, the connection of the two pumps would simplify the operation and increase the function security.

The doctor now can adjust $P_1$ and $Q_1$ independently; the necessary adjustment can be achieved automatically by readjustment or control of the suction pressure according to the following relationship wherein horizontal arrows pointing to the right indicate a relationship between the two variables positioned at the head and tail of the arrow and vertical arrows respectively pointing upward and downward signify respectively an increase and a decrease in the variable.

$P_1\uparrow \to P_2\uparrow$ $P_1\downarrow \to P_2\downarrow$     for $\Delta P_1 = \Delta P_2$ $Q_1\uparrow \to P_2\uparrow$ $Q_1\downarrow \to P_2\downarrow$     for $\Delta P_2 = -\frac{\Delta Q_1}{R_1 + R_2}$ For example, by increasing the value $P_1$, the arrangement has to increase $P_2$ consequently for the same amount, e.g. $\Delta P_1 = \Delta P_2$, to keep the actual value of $Q_1$ constant.

For the readjustment it is not necessary that $R_1$ and $R_2$ are known because the adjustment or control works in a direction toward the chosen operating point Ap of FIG. 3. If, for example, the pressure would not be changed, when increasing the set value $Q_1$, the control of the irrigation pump would maintain the preset pressure $P_1$ and thus, the actual value of the irrigation flux $Q_1$ would decrease, because the available pressure difference $P_1$–$P_2$ is not sufficient for the achieved increased flow (constant-pressure operating method). On the other hand when reducing $Q_1$ the pressure $P_1$ would fall (constant-flow-operating method), if the suction pressure $P_2$ or the suction flow $Q_2$ are not readjusted or controlled correspondingly.

The characteristic line (a) of a pump which is shown in FIG. 3 represent a pair of values (P, Q), which can be maximally reached by a given pump. This means, that the pump can reach arbitrary pairs of values, which lie over and beyond the characteristic line of the pump. Like in the other case, in which the pressure and the flow of a pump is regulated, the characteristic line (b) of the nominal values $P1_{T,set}$, and $Q_{1,set}$ can be obtained. At the point of crossing the characteristic line (b) by the characteristic line (c) of the fluid system (containing the inline—and outline tubes and also instruments), there is the actual working point (AP), which defines the effective values of pressure and flow. The pressure $P_{2,set}$ corresponds to the suction pressure of the suction pump, which is regulated automatically in this case such that the working point (AP) is always placed in the break point of the characteristic line (b). For example, the characteristic lines (b*) and (b**) are drawn with dotted lines, which shows the changing of the characteristic line (b), if the user increases (b*) respectively decreases (b**) the flux-nominal value $Q_{1,set}$ changes. In the first case it can be seen that the working point varies from the break point, that means that the flow-effective value $Q_{1,act}$ remains unchanged nevertheless the flow-nominal value $Q_{1,set}$ is changed. To reach the intended new working point $AP^*_1$, the suction pressure $P_{2,set}$ has to be increased appropriate to the value $P^*_{2,set}$. In the second case, in which the flow-nominal value is decreased to the value $Q^{}_{1,set}$, the working point varies to the point $AP_2$, that means the actual value of the flow follows the nominal value, but therefore the actual value of the irrigation pressure is decreased unwanted ($P^{}_1$, act). In this case the suction pressure $P_{2,set}$ has to be decreased to the value $P^{}_{2,set}$ to reach the new working point $AP^{}_2$ in the break point of the new characteristic line (b**). In a similar way it can be explained with this drawing the cases which are described hereinafter involving regulation of $P_1$ and $Q_1$. If the suction or irrigation line for example is broken, the gradient of the characteristic line (c) will be changed; due to the infinite flow resistance the characteristic line will become vertical, that means the effective-flow $Q_{1,act}$ decreases to zero, whereby the actual effective-pressure remains constant, identical to $P_{1,set}$.

When interrupting the irrigation line, the flow $Q_1$ is consequently reduced to zero due to the constant pressure regulation. This process causes a corresponding reduction of the suction pressure in response to the stopping of the suction drainage so that an undesirable emptying of the body cavity can be avoided.

If the suction drainage line is interrupted (i.e. by clogging with tissue particles) the rising pressure of $P_o$ can be reduced by a quick switching-off of the irrigation which is because of the reduced suction flow $Q_2$. Thus, an undesirable emptying of the suction line is avoided which would, if necessary, impede the elimination of the clogging.

Figure 4:
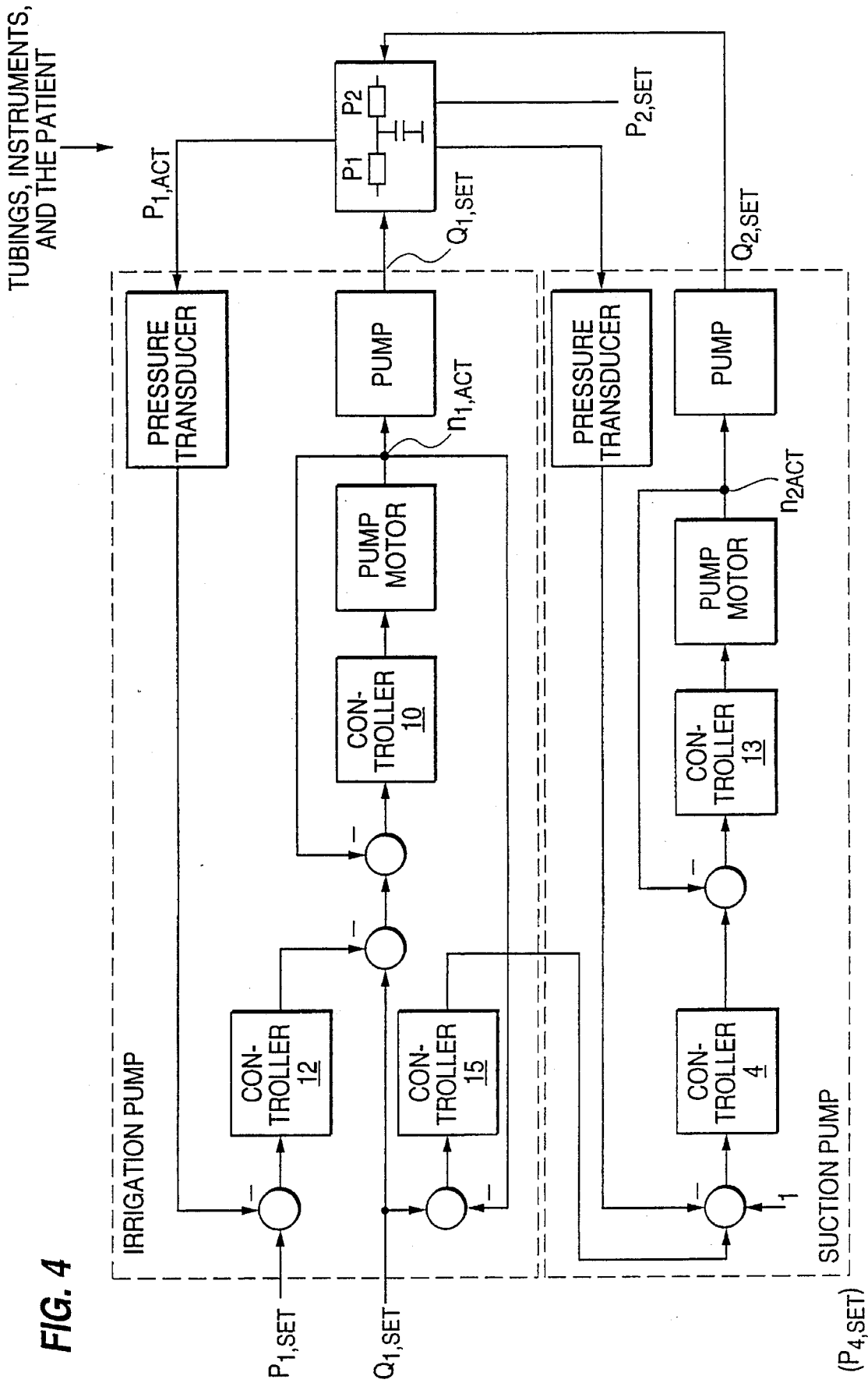
FIG. 4 illustrates control circuits of the irrigation and the suction pumps.

FIG. 4 shows an example of control circuits of the irrigation and the suction pump having a superior "master-slave" arrangement (controller 15). Principally, FIG. 4 illustrates a multi-stage cascade-controlling system. The controller 10 regulates the revolutions per minute and, therefore, the flow of the irrigation pump. The controller 12 is master to the controller 10 and regulates the irrigation pressure $P_1$. Similar functions exist for the controllers 13 and 14 of the suction pump. In the case of using a vacuum pump for the suction pump instead of a roller pump, the controller 13 is turned off. Finally, the controller 5 is the master controller which regulates the suction pump independently of the nominal values $P_{1,set}$ and $Q_{1,set}$, by giving the necessary suction pressure nominal value $P_{2,set}$.

While the invention has been described in terms of a preferred embodiment it should be understood that numerous modifications may be made thereto without departing from the spirit and scope as defined in the appended claims.

We claim:

1. A device for the irrigation of a body cavity comprising:

two pumps, one of the pumps operating as an irrigation pump and another of the pumps operating as a suction drainage pump, the two pumps being connectable with the body cavity to be irrigated via suction and drainage conduits which are placed into the body cavity in an endoscopic instrument so that a simultaneous irrigation and suction drainage of the body cavity is performed;

a pressure sensor unit; and a control means for controlling the two pumps with the pressure sensor unit having two pressure sensors, one of the two pressure sensors detecting pressure of the irrigation pump and another of the two pressure sensors detecting pressure of the suction drainage pump with output signals produced by the two pressure sensors being applied to the control means with the control means controlling the two pumps in a master-slave operation causing the suction drainage pump to be regulated based on the output signals of the two pressure sensors as well as a set r.p.m. of the irrigation pump in response to adjustment of the irrigation pump.

2. A device according to claim 1 wherein:

the pressure sensors are connected in fluid communication with the two pumps.

3. A device in accordance with claim 2 wherein:

the two pumps are connected with each other directly with a control line.

4. A device according to claim 2 wherein:

the pressure sensors detect the pressure respectively in an irrigation and in a suction drainage line.

5. A device according to claim 4 wherein:

the control means regulates the suction drainage pump to have a settable pressure said suction drainage conduit.

6. A device in accordance with claim 4 wherein:

the pumps are peristaltic pumps.

7. A device in accordance with claim 6 wherein:

the control means derives a flow resistance from the output signals of the two pressure sensors and from irrigation flux, which is proportional to the r.p.m. of the peristaltic irrigation pump, when there is no leakage within the body cavity.

8. A device according to claim 2 wherein:

the control means regulates the suction drainage pump to have a settable pressure said suction drainage conduit.

9. A device in accordance with claim 2 wherein:

the pumps are peristaltic pumps.

10. A device in accordance with claim 9 wherein:

the control means derives a flow resistance from the output signals of the two pressure sensors and from irrigation flux, which is proportional to the r.p.m. of the peristaltic irrigation pump, when there is no leakage within the body cavity.

11. A device according to claim 1 wherein:

the pressure sensors detect the pressure respectively in said irrigation and in said suction drainage line.

12. A device according to claim 11 wherein:

the control means regulates the suction drainage pump to have a settable pressure said suction drainage conduit.

13. A device in accordance with claim 11 wherein:

the pumps are peristaltic pumps.

14. A device in accordance with claim 13 wherein:

the control means derives a flow resistance from the output signals of the two pressure sensors and from irrigation flux, which is proportional to the r.p.m. of the peristaltic irrigation pump, when there is no leakage within the body cavity.

15. A device in accordance with claim 11 wherein:

the two pumps are connected with each other directly with a control line.

16. A device according to claim 1 wherein:

the control means regulates the suction drainage pump to have a settable pressure said suction drainage conduit.

17. A device in accordance with claim 1 wherein:

the pumps are peristaltic pumps.

18. A device in accordance with claim 17 wherein:

the control means derives a flow resistance from the output signals of the two pressure sensors and from irrigation flux, which is proportional to the r.p.m. of the peristaltic irrigation pump, when as there is no leakage within the body cavity.

19. A device according to claim 1 further comprising:

a weighing unit for detecting a weight difference between a storage container for an irrigation fluid pumped by the irrigation pump and a collection container for the irrigation fluid suction drained from the body by the suction drainage pump with an output signal of the weighting unit being coupled to the control means for balancing the weight of fluid in the containers.

20. A device in accordance with claim 1 wherein:

the two pumps are connected with each other directly with a control line.

* * * * *